(12) United States Patent
Thomas

(10) Patent No.: US 9,996,923 B2
(45) Date of Patent: Jun. 12, 2018

(54) METHODS AND APPARATUSES FOR DERMATOLOGICAL FEATURE TRACKING OVER MULTIPLE IMAGES

(71) Applicant: Canfield Scientific, Incorporated, Fairfield, NJ (US)

(72) Inventor: Mani V. Thomas, Raritan, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 102 days.

(21) Appl. No.: 15/136,906

(22) Filed: Apr. 23, 2016

(65) Prior Publication Data

US 2016/0314585 A1 Oct. 27, 2016

Related U.S. Application Data

(60) Provisional application No. 62/152,529, filed on Apr. 24, 2015.

(51) Int. Cl.
| | |
|---|---|
| G06K 9/00 | (2006.01) |
| G06T 7/00 | (2017.01) |
| A61B 5/00 | (2006.01) |
| G06K 9/46 | (2006.01) |
| G06K 9/62 | (2006.01) |
| G06K 9/66 | (2006.01) |

(Continued)

(52) U.S. Cl.
CPC .......... *G06T 7/0012* (2013.01); *A61B 5/0077* (2013.01); *A61B 5/444* (2013.01); *G06K 9/00362* (2013.01); *G06K 9/3233* (2013.01); *G06K 9/46* (2013.01); *G06K 9/6215* (2013.01); *G06K 9/66* (2013.01); *G06T 7/0016* (2013.01); *G06T 7/246* (2017.01); *G06K 2009/4666* (2013.01); *G06T 2207/30088* (2013.01)

(58) Field of Classification Search
None
See application file for complete search history.

(56) References Cited

U.S. PATENT DOCUMENTS 7,457,659 B2 11/2008 Maschke
7,894,651 B2 * 2/2011 Gutkowicz-Krusin A61B 5/0059
382/128

(Continued)

FOREIGN PATENT DOCUMENTS

| | | |
|---|---|---|
| EP | 2733664 A1 | 5/2014 |
| WO | 2013144186 A1 | 10/2013 |
| WO | 2015175837 A1 | 11/2015 |

OTHER PUBLICATIONS

International Search Report and Written Opinion of the ISA, PCT/US2016/029081, dated Jul. 11 2016.

(Continued)

*Primary Examiner* — Tahmina Ansari
(74) *Attorney, Agent, or Firm* — Brosemer, Kolefas & Assoc., LLC

(57) ABSTRACT

Methods and apparatus are disclosed that assist a user such as a doctor to track changes that occur in features of a subject's skin as the skin features evolve over time. Such a tracking can be done for images captured under different imaging/lighting modalities, by different image capture devices, and/or at different points in time. Methods and apparatus to automatically identify and track the unconstrained appearance/disappearance of skin features are disclosed.

25 Claims, 10 Drawing Sheets

(51) Int. Cl.
    *G06K 9/32*         (2006.01)
    *G06T 7/246*      (2017.01)

(56) References Cited

U.S. PATENT DOCUMENTS

| | | | |
|---|---|---|---|
| 2007/0260230 A1* | 11/2007 | Youngquist | A61B 18/203 606/9 |
| 2008/0214907 A1* | 9/2008 | Gutkowicz-Krusin | A61B 5/0059 600/306 |
| 2009/0118600 A1* | 5/2009 | Ortiz | A61B 5/0064 600/306 |
| 2012/0078113 A1* | 3/2012 | Whitestone | A61B 5/0077 600/474 |
| 2012/0206587 A1 | 8/2012 | Oz et al. | |
| 2015/0097957 A1* | 4/2015 | Crona | G06K 9/00771 348/149 |
| 2016/0314585 A1* | 10/2016 | Thomas | G06T 7/0012 |
| 2017/0074640 A1* | 3/2017 | Cable | G01B 9/02083 |

OTHER PUBLICATIONS

Third Party Observation submitted by Anonymous in PCT/US2016/029081 on Aug. 21, 2017.

Ulf Elwanger, Screening-Hilfe fur die Melanomfruherkennung, Deutsches Arzteblatt-Praxis, Nov. 4, 2005 (German language article; statement of relevance in Third Party Observation listed above).

Manual DatInf MoleExpert macro, 2007.

* cited by examiner

METHODS AND APPARATUSES FOR DERMATOLOGICAL FEATURE TRACKING OVER MULTIPLE IMAGES

RELATED APPLICATIONS

This Application claims priority from U.S. Provisional Patent Application No. 62/152,529, filed Apr. 24, 2015 and incorporated herein by reference in its entirety.

BACKGROUND INFORMATION

In the field of dermatology, the diagnosis of skin conditions has traditionally depended on a one-on-one, touch-and-feel form of consultative paradigm. While this form of interaction has helped the dermatologist to visually identify pathological conditions, the advent of technology has helped augment the consultation with additional meta-information that vastly improves the diagnosis. For example, devices such as hand-held dermatoscopes are now fairly common in a typical dermatologist's practice. Moreover, depending on the scale of operation, the dermatologist might have access to an entire spectrum of devices, from dermatoscopes to multi-camera, multi-modality, whole-body systems, to help with the end goal of providing better patient care.

When studying any ailment, the concept of a "delta" between two observations that are separated in time is critical in understanding how the pathology is changing. In some cases, the observed change might be extremely gradual, and may require multiple visits over a prolonged period of time for accurate diagnosis. Other conditions might erupt/subside in a very short time. In either case, the doctor would have to observe the patient at different timepoints to be able to generate an accurate diagnosis of the ailment. When studying dermatological conditions, in particular, visual changes in and around the vicinity of the area of interest play a crucial role. Like other pathologies, different types of dermatological conditions have different rates of progression and spatial extents. Some skin conditions (e.g., a skin rash) are localized whereas others (e.g., pigmented or non-pigmented skin lesions) could be distributed all over the body. In some observed cases, over 2,000 lesions have been found distributed all over the patient's body. In terms of their evolution, some skin lesions are known to have a very slow rate of growth, while others have been known to be very aggressive. Given this spatio-temporal extent of skin lesions, observing, analyzing, and classifying them, such as benign or malignant, can be overwhelming. Moreover, the consequences of missing or misclassifying skin lesions can be quite serious.

In most cases, malignancy tends to manifest itself as changes in texture, color, or size of the lesion over time. It is therefore essential for the dermatologist to observe this evolution over time. However, identifying, annotating, and tracking thousands of lesions across a number of patient visits is a daunting task, both in terms of effort and liability. For example, even for a single timepoint (e.g., office visit), manual annotation of multiple skin lesions located over the patient's body often entails several hours of painstaking work for the dermatologist's support staff. In addition, for each subsequent visit, the doctor and/or their staff would need to manually tag the lesions and build a lesion-to-lesion correspondence. A specialist would then try to identify changes in the lesions in order to classify each of the lesions as malignant or benign, and to decide which to excise or treat by other means. On the whole, the entire exercise is extremely strenuous and expensive, both from the doctor's as well as the patient's perspective.

Other skin pathologies like acne, rosacea, psoriasis, etc. entail similar and equally tedious diagnostic procedures. The dermatologist is typically presented with an abnormal observation at timepoint 1 (the baseline), and over the life of the pathological condition, continually tries to observe and evaluate changes. In order to maintain spatial and/or temporal coherence, the dermatologist might manually tag each condition, or perhaps use photo documentation to help organize the patient's records. However, the onus of noticing the relevant changes and evaluating their significance falls completely on the doctor's shoulders. As can be imagined, any recourse to automating this process as a diagnostic aid for the dermatologist would lead to improved efficiencies in time, effort and detection rate (i.e., reduction in false negatives due to missed detection), while leading to an overall reduction in cost.

When we consider the possibility that new skin features might spontaneously appear or disappear, there is an added challenge of evaluating these new formations, or the lack thereof, and evaluating their consequence to the health of the patient. Manually tracking and/or documenting the unconstrained appearance or disappearance of skin features makes the entire workflow all the more challenging and error-prone.

It bears noting that when observing human subjects, change detection is particularly challenging. Changes in a subject's perceived appearance result from a complex combination of factors such as age-specific variations, pathological changes, physical movement, physical appearance variations, etc., in addition to changes in lighting conditions and differences between the devices with which the images are captured. This is further complicated when images are captured under different imaging modalities (e.g., cross-polarized, parallel-polarized, fluorescence, etc.), which result in images that look very different from images captured under standard white-light illumination. Comparing images across time, modality, and/or capture devices is thus a very challenging problem. There is a need therefore, for methods and apparatus to track the perceived changes between images, both across time, lighting modalities, and/or capture devices.

SUMMARY OF THE DISCLOSURE

The present disclosure sets out methods and apparatus for tracking changes that occur in skin features as the skin features evolve over time. Such a tracking can be done for images captured under different imaging/lighting modalities, by different image capture devices, and/or at different points in time. In addition, methods and apparatus to automatically identify and track the unconstrained appearance/disappearance of skin features are also provided, a process that is considered extremely difficult and tedious. This disclosure also provides methods and apparatus to connect images of a subject, collected over multiple timepoints or across different imaging/lighting modalities, so as to create a visualization of a given skin condition's life cycle (i.e., from onset to termination). This disclosure also provides methods and apparatus to connect images of subjects, collected over multiple timepoints or across different imaging/lighting modalities, so as to collect the data for subsequent spatial and/or temporal data analysis.

Several illustrative embodiments of the present disclosure are primarily adapted to analyze images of human subjects, specifically to study skin features, pathological skin conditions, or any other external features of the human body that are observable in an image, or in a sequence of images.

These and other aspects of such systems and methods and exemplary variants thereof are described in greater detail below.

DETAILED DESCRIPTION

Figure 1:
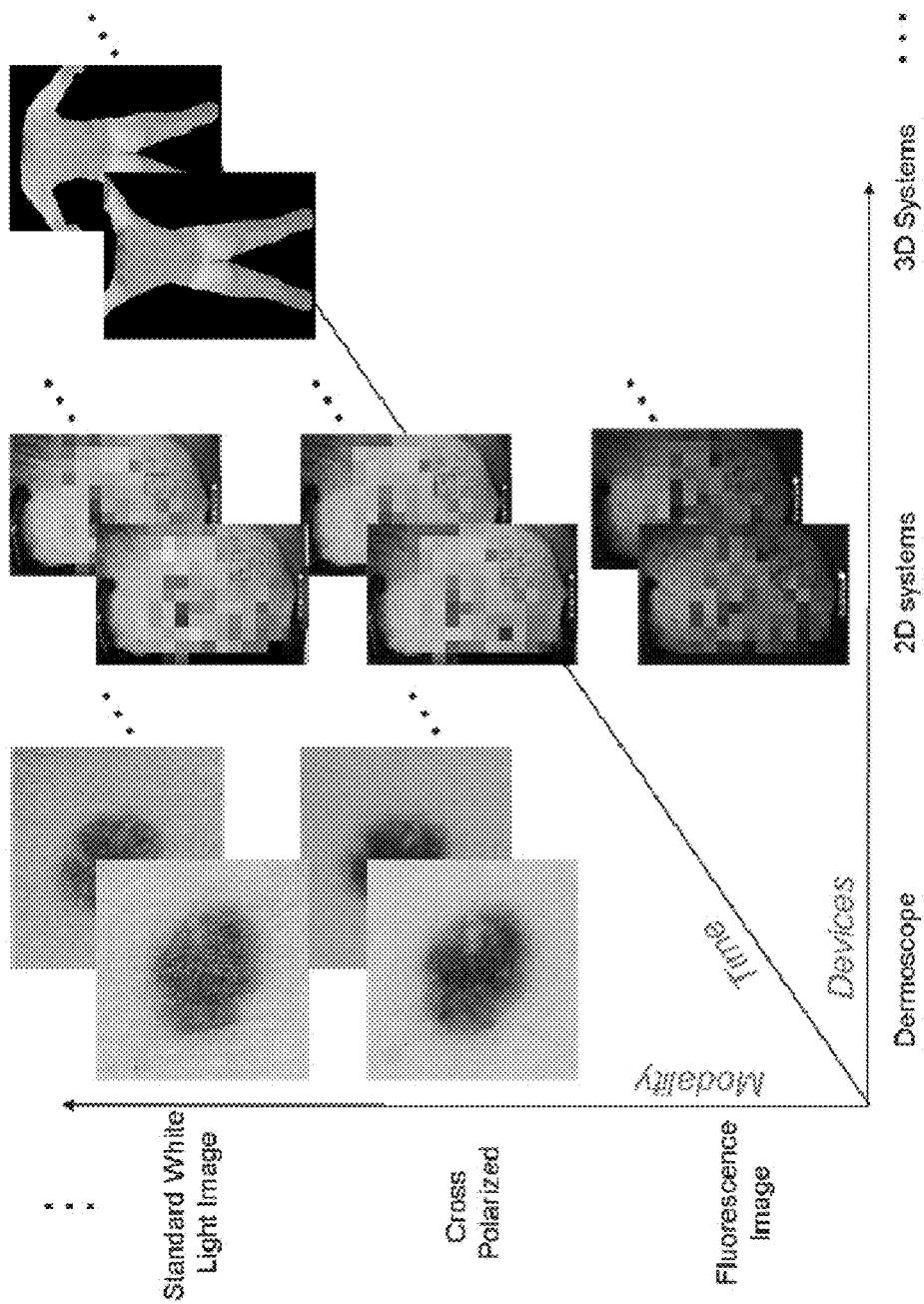
FIG. 1 is a graphical depiction of three exemplary dimensions over which images to be compared may vary, including image modality, time of image capture, and image capture device.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, and the like represent various processes which may be substantially represented in computer readable medium and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flow chart elements or other elements indicating performance of process steps and/or textual description. Such modules may be executed by hardware that is expressly or implicitly shown.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture and a 3D volumetric image data might represent a stack of 2D images that represent a 3D volume of the object being imaged, such as a stack of MRI images.

Skin features or pathological conditions may include, for example, wrinkles, spots, pores, scars, tattoos, moles, skin lesions, nevi, acne, etc.

In some cases, different skin features are often related. Related feature can be visually very distinct but are associated with one another as manifestations of the underlying process that taking place in the skin. Examples of related features include: a skin lesion (observable in a standard/white light image) and erythema (observable in a cross-polarized image) often present around the lesion indicative of blood; a comedone (black/white head) that is observed as a strong fluorescence signal in a green image seen with a hemoglobin blob that is visible in a RBX red image; and an acne pustule in a standard/white light image seen with the co-located topography from a 3D surface model.

Skin images may be captured on any device that either captures the full human body or any subsection thereof, such as the face. Image capture devices may also include hand-held or mounted point-and-shoot or DSLR cameras, mobile cameras, frontal or rear-facing smart-device cameras, dermatoscopes (e.g., Canfield Scientific Inc.'s VEOS), 2D skin imaging systems (e.g., Canfield Scientific Inc.'s VISIA), 3D human body imaging devices (e.g., Canfield Scientific Inc.'s VECTRA), 3D Total Body systems (e.g., Canfield Scientific Inc.'s WB360), among others. Additionally, images can also be captured across various modalities such as, for example, standard white light, cross polarized, parallel polarized, and/or fluorescence. In this disclosure, images collected across different modalities are collectively termed multi-modal images.

In automating the processes of documenting and analyzing skin conditions, several typical scenarios warrant consideration. The first scenario is the analysis of a single image of the subject at a given timepoint. This single-timepoint analysis may involve the use of automatic segmentation and visualization algorithms, and corresponds to the manual annotation/tagging of skin features typically carried out by a dermatologist's staff. A single timepoint is generally an instant or a short period of time during which no perceptible change in skin condition would typically occur, such as the duration of a single skin examination, for example.

Another scenario involves comparing two or more images captured at different timepoints and/or using different imaging devices and/or modalities, such as for the purpose of building a spatial and/or temporal map of skin features in the images. The establishment of feature correspondences across multiple images would provide an automated alternative to the manual tagging and tracking of skin features by practitioners.

An exemplary technique in accordance with the present disclosure works on a pair of images at a time. In the case of an image sequence, an exemplary process is repeated on all or some combination of image pairs, and the results can be fused together to produce the final output. Such fusion may entail combining the information (e.g., raw pixel values or any derived data from the pixels) so that the final combination is better than any one individual component alone. Methods of fusion can include, but are not limited to, simple averaging of the data to complex voting schemes. The sequence of images can represent two or more images captured under different imaging modalities, at different times, with different devices, or any combination of these three dimensions of variation.

The aforementioned three dimensions of variation are depicted graphically in FIG. 1, namely, 1) the imaging devices that are used, 2) the imaging modalities that the subject is captured under, and 3) the timepoints at which the images are captured.

Image pairs can also be formed from image frames of a video sequence, which can be considered an example of images captured at different times.

In the aforementioned situations, exemplary embodiments can preferably receive user input to manually annotate/segment features or other areas of interest (AOI) in one or more of the images and have the system automatically transfer the annotation/segmentation across the images from the same capture set, where a capture set might include 2D images, 3D surfaces and/or 3D volumetric images of the same subject collected across different image modalities/lighting and/or across different time points.

We have discovered that the complex motion that characterizes the movement of a human subject's skin from one image to another can be decomposed into a hierarchy of motion types, starting from the global scale, which can be described using very few parameters, to a completely unconstrained local deformation model with two or more parameters at every pixel location of the image. When working with human subjects, an additional pose estimation step may be required or desirable before computing the global scale motion.

The macro perspective is that complex motion can be filtered out by iteratively increasing the number of parameters required to model the motion. In an exemplary implementation, the number of models can be divided into four sub-blocks: 1) pose estimation, 2) global scale motion estimation, 3) intermediate scale motion estimation, and 4) fine scale motion estimation. Such an implementation will now be described with reference to FIG. 2.

Figure 2:
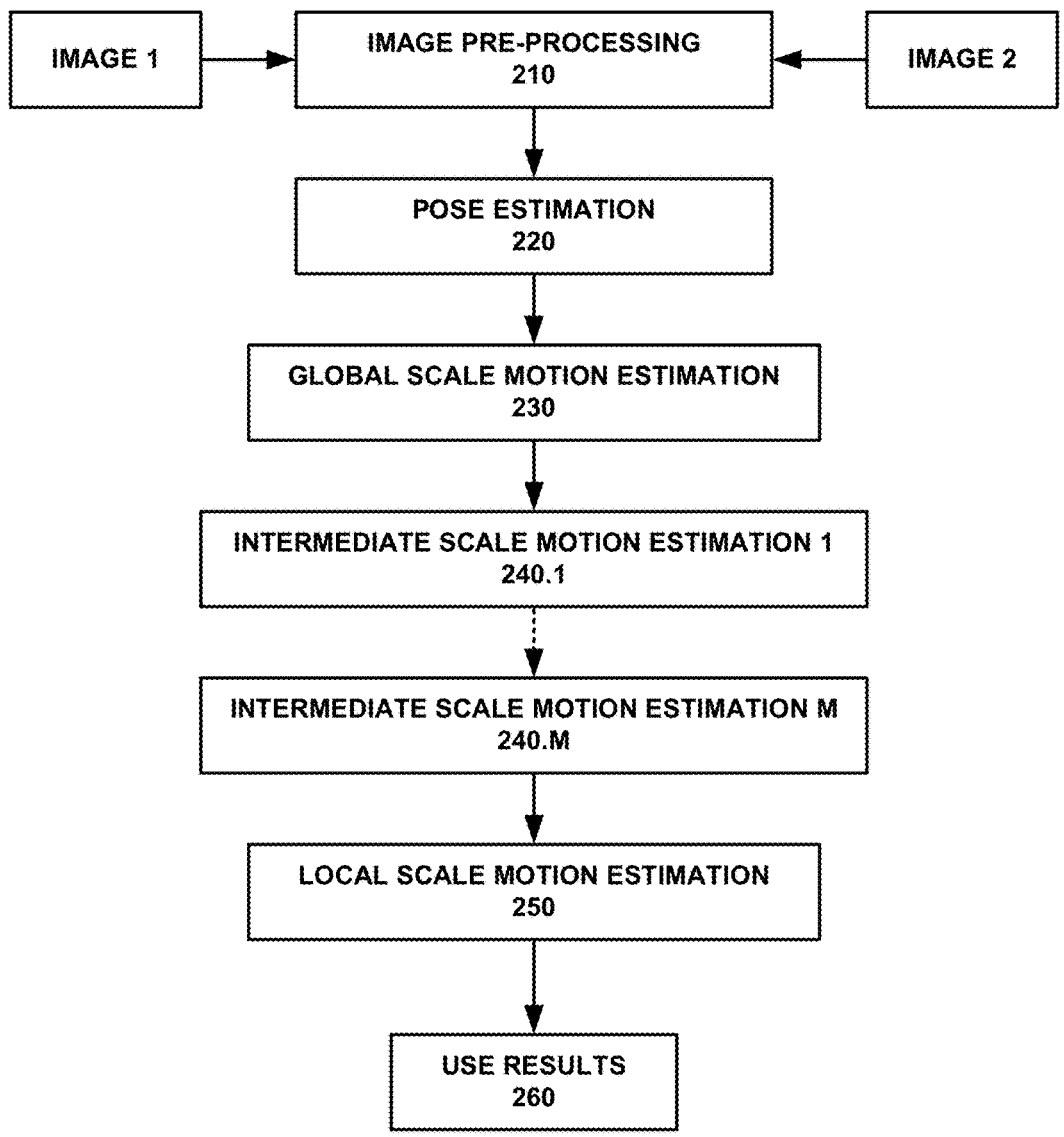
FIG. 2 is a schematic representation of an exemplary hierarchical motion estimation arrangement in accordance with the present disclosure.

FIG. 2 is a schematic representation of an exemplary arrangement for performing hierarchical motion estimation given a pair of input images that may be captured at two timepoints, using two different imaging modalities, and/or with two different image capture devices. As mentioned, these three aspects of variation between images of an image pair are graphically depicted in FIG. 1.

As shown in FIG. 2, images 1 and 2 are first subjected to pre-processing 210. Pre-processing may include, for example, any pixel-based operations such as image filtering, histogram equalization or color correction. Pre-processing may also include noise/artifact removal, image cropping, etc., that may be required or desirable to adjust the input images to account for variations in capture conditions, such as lighting, color, saturation, etc. Pre-processing can also be used to improve the performance of the motion estimation to follow. Pre-processing can be omitted, however, if there are no significant variations in the capture conditions and/or the images as captured are of sufficient quality for the subsequent processing steps.

Following pre-processing 210, pose estimation 220 estimates the pose of the human subject from the input images that were captured. Pose estimation algorithms for generic images are described, for example, in A. Toshev at al., "DeepPose: Human Pose Estimation via Deep Neural Networks", IEEE Conference on Computer Vision and Pattern Recognition, 2014, and Y. Yang et al., "Articulated pose estimation with flexible mixtures of parts", Computer Vision and Pattern Recognition (CVPR), 2011. In exemplary embodiments of the present disclosure, these algorithms can be further constrained and modified to use a feed-forward neural network applied to shape contexts. The primary purpose of pose estimation 220 is to determine the same anatomical sub-section of the body observed in the pair of input images. Consider the case in which a subject has their arms extended out in image 1 but has them raised in image 2. In such a situation, a correspondence between the images of the same observed physical area is identified. Human pose estimation helps identify this correspondence. Using the estimated pose, a sub-section that corresponds to the right arm, for example, can be extracted from the two images and used in the subsequent models.

Pose estimation 220 would typically only be required in conjunction with input images that cover a large field of view, such as those captured with a 3D total body imaging device. In cases where the region being analyzed is location-constrained, such as with a dermatoscope or a 2D imaging device like Canfield Scientific Inc.'s VISIA, pose estimation 220 can be omitted.

Following pose estimation 220, global scale motion estimation 230 estimates the "global scale" motion between the pair of input images. In the case of 2D images, motion can be determined as the 2D projection of the 3D movement of a collocated subsection on the human subject. Moreover, "collocation" presupposes the prior application of pose correction 220 or location-constrained imaging.

In exemplary embodiments, global scale motion is approximated using a simple parametric motion model having a relatively small (e.g., <10) number of parameters. These parameters describe the observed combination of translation, rotation, scale, and/or shear. A purpose of global scale motion estimation 230 is to estimate these parameters robustly.

To estimate the parameters, global scale motion estimation 230 can use a set of correspondences obtained by comparing spatial/spectral image features (e.g., gradients, corners, oriented histograms, Fourier coefficients, etc.) Outliers from the correspondences thus obtained are preferably filtered out, such as by using a robust scheme like RANSAC or LMedS. The model parameters can be subsequently computed using model fitting strategies. Several suitable techniques exist. See e.g., C. Tomasi et al., "Detection and Tracking of Point Features", Pattern Recognition 37: 165-168, 2004; D. G. Lowe, "Distinctive Image Features from Scale-Invariant Keypoints", Intl. Journal of Comp. Vision 60 (2): 91-110, 2004; E. Rublee et al., "ORB: an efficient alternative to SIFT or SURF", IEEE Intl. Conf. on Comp. Vision (ICCV), IEEE, 2011; B. S. Reddy et al., "An FFT-based technique for translation, rotation, and scale-invariant image registration", Trans. Img. Proc. 5, 8, 1266-1271, Aug. 1996; M. Thomas et al., "A robust phase-correlation based motion estimation algorithm for PIV", Measurement Science and Tech., 16(3), 865-877, 2005.

Once the global motion model parameters have been estimated, the two images can then be aligned into a common global coordinate system and passed along to the next block.

The pair of global motion compensated images are passed as inputs to an intermediate scale motion estimation 240. Like global scale motion estimation 230 described above, intermediate scale motion estimation 240 can also use a parametric motion model to estimate the movement in the pair of input images. The parametric model for intermediate scale motion, however, will likely entail a much larger number of parameters than that of the global scale motion model. While the number of parameters used in a global scale motion model may be fixed, the number of parameters in the intermediate scale motion model may be based on the number of correspondences used. For example, models such as the Thin Plate Spline use a combination of weighted local deformations extracted from the correspondences, and a simple parametric global transformation to describe the overall motion. See, e.g., F. L. Bookstein, "Principal Warps: Thin Plate Splines and the Decomposition of Deformations", IEEE Trans. Pattern Anal. Mach. Intelligence, 11, 567-585, 1989.

As with global scale motion estimation 230, intermediate scale motion estimation 240 can use image features to build a collection of correspondences between the image pairs. In an exemplary implementation, the correspondence set is reduced to the inliers using an outlier rejection procedure derived from RANSAC. See, e.g., Q. H. Tran, et al., "In defence of RANSAC for outlier rejection in deformable registration", 12$^{th}$ European Conf. on Computer Vision 2012, Vol. 7575, 274-287, 2012. This produces a set of outlier-free sparse correspondences, which might, however, occur in dense, non-uniform clusters. To improve the convergence of the intermediate scale motion model, these correspondences can be sampled to maintain spatial diversity. This sampling can be conducted using one of several possible techniques including, for example, grid-based sampling, Poisson disk sampling, stratified sampling, etc. Using the sampled inlier correspondences, this model estimates the weights assigned to each of the correspondences so as to compute the parametric transformation.

Intermediate scale motion estimation 240 can be carried out using one parametric model or multiple parametric models. As depicted in FIG. 2, intermediate scale motion estimation 240 can be decomposed into one or more components (240.1-240.M) that can be daisy-chained together to produce the composite set of parameters that describe the intermediate scale of motion.

In some cases, it may be possible for the intermediate scale motion model to replace or incorporate the functionality of the global scale motion model. These cases typically arise when the observed motion is composed of large, non-rigid deformations and global motion. In such a situation, the use of the global motion model alone lacks the expressiveness to model the non-rigid deformations, and the use of an intermediate scale motion model is better suited for estimating the combined set of parameters. An example of such a case arises when analyzing images of a subject's back and their arms are extended horizontally in one image and vertically in the other. In this case, the area around the shoulder blades moves up, the lower section of the back tends to stay in place and the skin in the center of the back gets stretched out. In such cases, using an intermediate scale motion model would be better at approximating the motion than using a global scale model.

After intermediate scale motion estimation 240, local scale motion estimation 250 estimates the finest scale of non-rigid deformation occurring between the pair of input images. The non-rigid deformation can be treated as being composed of a horizontal and a vertical displacement at every pixel in the image. This displacement could represent a linear displacement, such as a translation, or could represent higher order models like affine, quadratic, or other polynomial models, perspective, etc. Given the possible degrees of freedom, estimation of this displacement is typically an ill-constrained problem (i.e., having fewer equations to solve than the number of variables). If, however, additional constraints are provided, such as using the intermediate scale motion model as a predictor or using smoothness constraints (e.g., no discontinuities, motion is smooth within a localized area, the motions of neighboring pixels are similar, etc.), an exemplary local motion model can be tuned to generate accurate estimates of the local deformation. The accuracy of local scale motion estimation 250 thus depends on the accuracy of the preceding blocks. The better the preceding blocks are at compensating for larger motion, the lesser would be the estimation error in local scale motion estimation 250.

There are several algorithms that can be used within local scale motion estimation 250, including, preferably, the algorithm described in M. Thomas, et al., "High resolution (400 m) Motion Characterization of Sea Ice using ERS-1 SAR Imagery", Cold Regions Science and Technology, 52, 207-223, 2008. Regardless of the algorithm used, estimating fine scale motion is an important aspect of parameterizing the problem of change detection.

As with the previous blocks, local scale motion estimation 250 can function independently of the preceding blocks, especially when the images being processed are location-constrained. Take for example, the task of estimating the observed change between two dermoscopy images of the same skin feature captured at two different points in time. In this case, the local scale motion might be sufficient to align the two images together and to track the change that is observed.

The results of the aforementioned blocks, including the motion models determined thereby, can then be used at 260 in a variety of ways. For example, the results can be presented to the user (e.g., doctor) via a display device or stored in a storage device for analysis at a later time. The former use case can arise, for example, when comparing two images captured under different imaging modalities but within the same time frame, such as, for example, comparing a dermoscopy image of a skin feature to a 3D whole body image of the same subject for the purposes of automatically identifying and tagging the dermoscopy image to the corresponding skin feature on the 3D whole body image. The storage device could be used, for example, when analyses are batch processed and the results from various pair-wise analyses are consolidated together for use at a later time.

Figure 3:
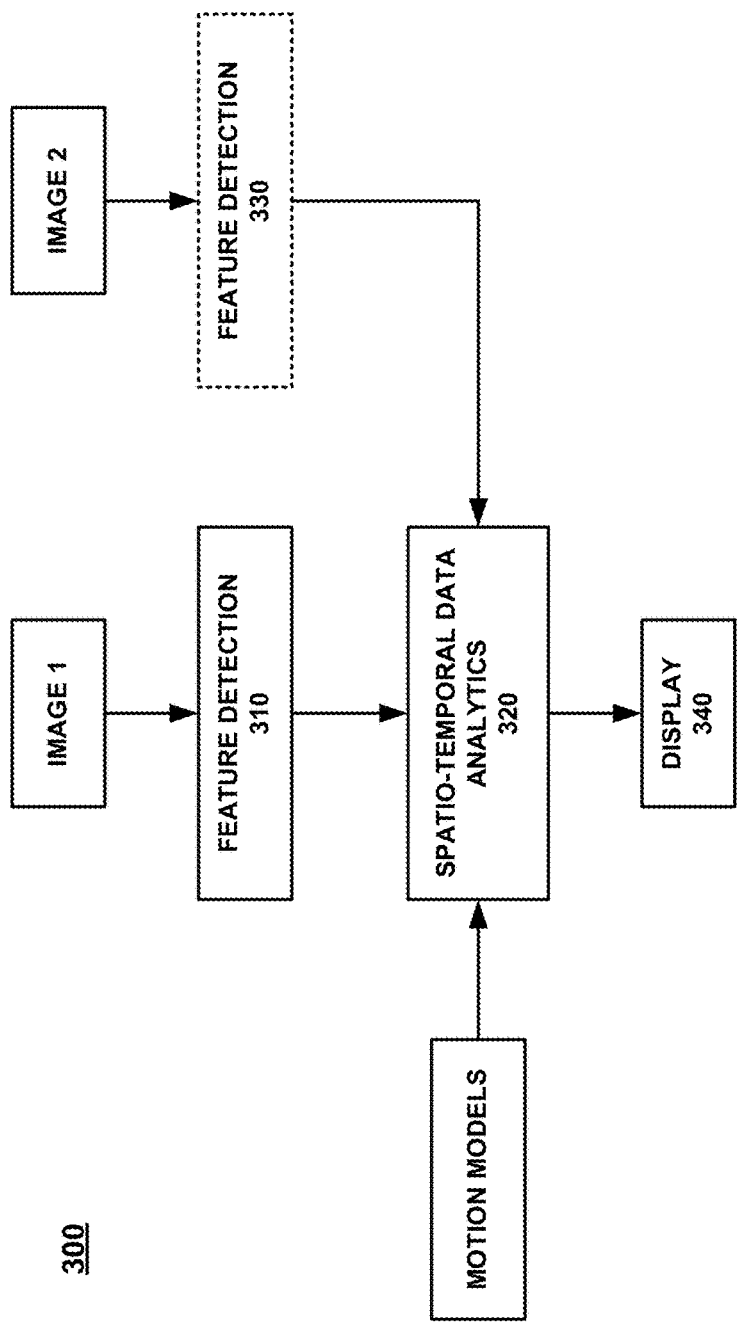
FIG. 3 is a schematic representation of an exemplary arrangement for performing spatio-temporal analysis in accordance with the present disclosure.

FIG. 3 is a schematic representation of an exemplary arrangement 300 for performing spatio-temporal analysis in accordance with the present disclosure.

In an exemplary implementation, the user selects for display a first one of the images in a pair of sequentially captured images. Preferably, the system is configured to allow the user to select either the earlier or later captured image of the pair. Feature detection 310 is then performed on the selected image. In exemplary embodiments, the user, such as with the use of a suitable graphical user interface (GUI), may specify on the selected image a region of interest (ROI) within which features are to be detected. In exemplary embodiments, the system can automatically or semi-automatically generate the ROI, such as, for example, an ROI of a selected anatomical region, such as the skin of the face. The specification of an ROI may be desirable where the selected image covers a large area or a complex area, such as the face, or includes more features than those in which the user is interested. A segmentation procedure can then be used to identify skin features in the specified ROI.

Spatio-temporal analytics block 320 then uses the parametric motion models determined as described above with reference to FIG. 2 to predict the location of the specified ROI and/or identified skin features in the second image of the image pair.

An additional feature detection 330 can be performed at the predicted ROI location in the second image to identify skin features of interest in the second image. Based on the spatial configuration of the skin features within the two ROIs and by using pixel measurements such as border, color, intensity, texture, etc., the correspondence of said skin features can be established for the pair of images. Alternatively, the user can identify the skin features in the first and/or second image, such as by use of the GUI. In this case, the segmentation performed by the system can be replaced by the identification made by the user.

Various exemplary methods of operation of arrangement 300 will now be described with reference to FIGS. 4 and 5A-5E.

Figure 4:
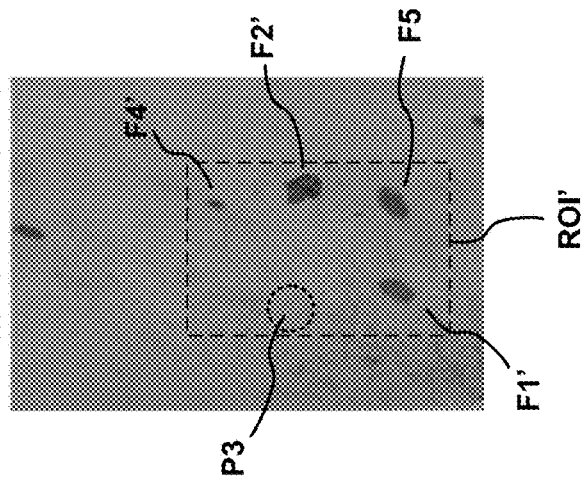
FIG. 4 shows a pair of images for illustrating aspects of the present disclosure.
Figure 4:
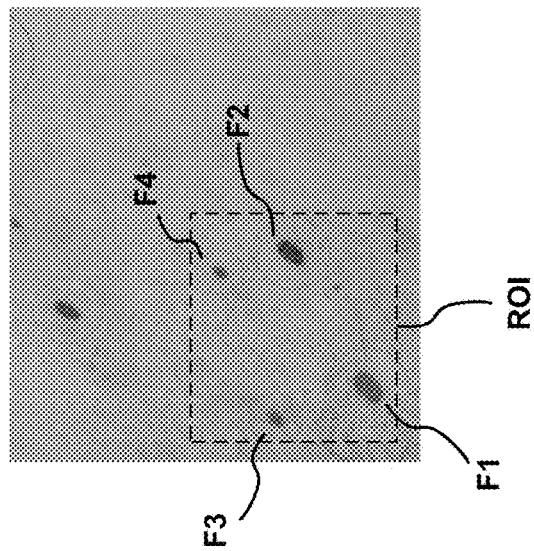

FIG. 4 shows an illustrative pair of input images captured at different timepoints, possibly with different devices. The area designated ROI in Image 1 corresponds to the area ROI' in Image 2. Similarly, skin features appearing as F1, F2 and F4 in Image 1 appear in Image 2 as F1', F2' and F4', respectively. Note the relative movement and lighting differences between the two images. Additionally, compare the appearances of features in the ROI of the two images. While feature appearances F1 and F4 appear substantially unchanged, F2 has changed shape and size, F3 has disappeared and F5 has appeared.

Figure 5A:
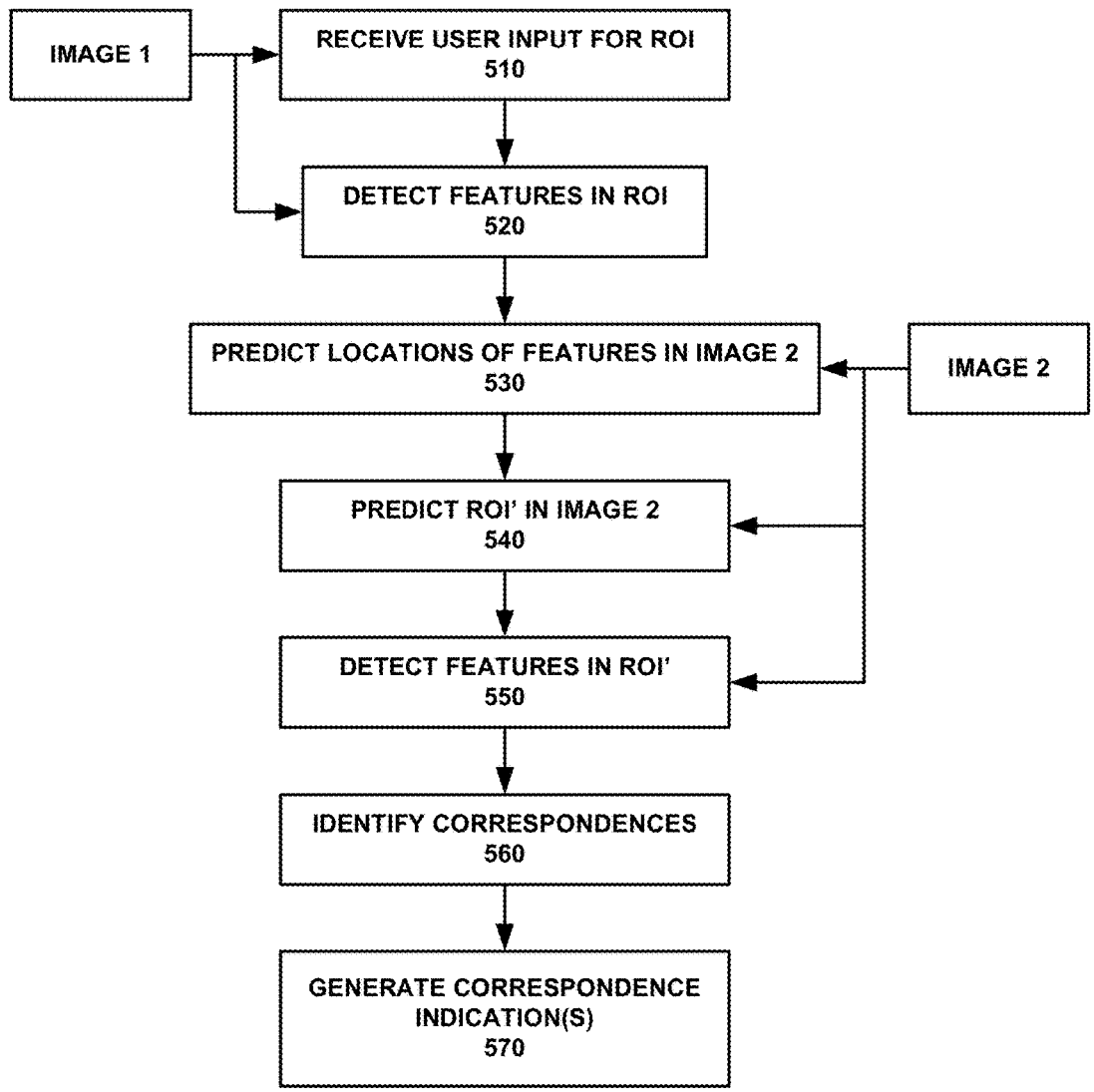
FIGS. 5A through 5E are flow charts illustrating various exemplary procedures in accordance with the present disclosure.

As depicted in the flow chart of FIG. 5A and with reference to FIG. 4, in an exemplary procedure in accordance with the arrangement 300 of FIG. 3, an exemplary system: at 510, receives input from the user specifying a ROI in the first image of the image pair; at 520 detects skin feature(s) (e.g., F1-F4) within the ROI in the first image; at 530 predicts the location(s) in the second image of the skin feature(s) detected in the first image; at 540 predicts the location in the second image of the ROI specified in the first image; at 550 detects skin feature(s) (e.g., F1', F2', F4') within the predicted ROI' in the second image; at 560 identifies any correspondence(s) between the skin feature(s) detected in the first image and the skin feature(s) detected in the second image, such as by a) comparing the predicted location(s) from step 530 with the location(s) of skin feature(s) detected in step 550, or by b) comparing the spatial arrangement of skin feature(s) detected in step 520 within the ROI in the first image to the spatial arrangement of skin feature(s) detected in step 550 within the ROI' in the second image; and at 570 generates an indication of any correspondence(s) identified (e.g., F1-F1', F2-F2', F4-F4') and/or an indication if any expected correspondence is missing in either direction (Image 1 to Image 2 or vice versa), so as to bring this to the user's attention.

With respect to 570, a correspondence can be deemed to be missing if no skin feature is detected at a location predicted at 530, such as in the case of feature F3 shown in FIG. 4, or if a feature is detected in image 2, at a location which was not predicted at 530, such as in the case of feature F5. Where a feature appears in one image and not the other, the expected location of the feature in the image in which it is missing can be predicted from the location of the feature in the image in which it appears. A search can then be performed at or proximate to the predicted location. The results of such a search may provide information suggesting an early onset, resolution, or otherwise significantly changed appearance of the feature, which may warrant further consideration.

Where a correspondence is identified, such as in the cases of features F1 and F2, the system can display the images so that when a user selects a feature in one image, its corresponding appearance in the other image will be highlighted, for example, or provide some other suitable indication of their correspondence, such as a line connecting the appearances, indicia with matching alphanumeric information, shapes and/or colors, or an isolated or magnified view of the corresponding appearances, among other possibilities.

Where a correspondence is found but there appear to be differences between the two appearances of the feature, indicia can be generated in accordance with the detected degree of change so as to alert and/or assist the user in prioritizing the potential significance of detected features. For example, green indicia can be used for correspondences displaying little or no change, yellow for correspondences with an intermediate degree of change and red for correspondences with a significant degree of change. Metrics and other information can also be displayed.

Where a correspondence is missing, as in the cases of F3 and F5, indicia can be generated to indicate those feature appearances in one image lacking a corresponding appearance in the other image and/or indicia in or around the predicted locations of the missing appearances (e.g., P3 in Image 2 of FIG. 4).

When displaying image pairs, it may be desirable to normalize the images in one or more respects (e.g., shape, size, orientation, brightness, etc.) so as to provide to the viewer a more equivalent comparison of the images. For example, in the illustrative images shown in FIG. 4, Image 2 can be warped so that the shape of ROI' matches that of ROI in Image 1. Additionally, the brightness levels of the two images can be equalized, among other possible adjustments that can be made to either or both images.

Figure 5B:
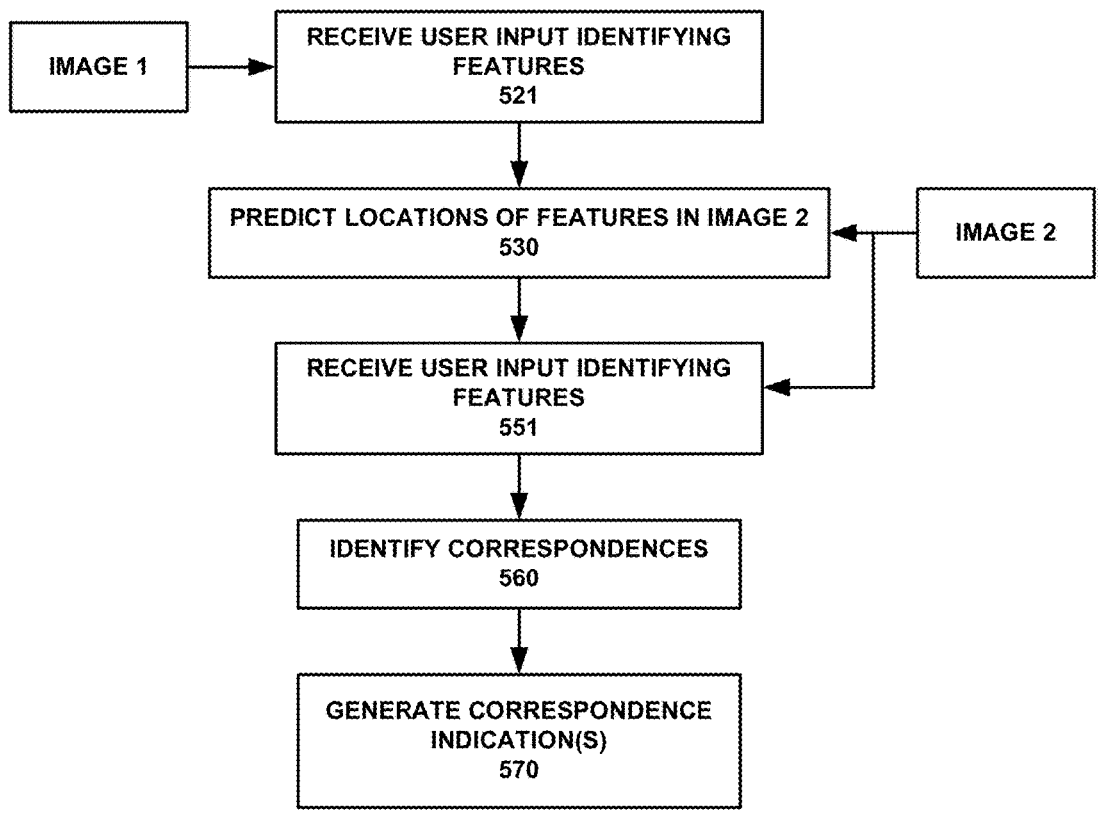

In further exemplary procedures, one or more of steps 520, 550 and 560 can be performed with user input and one or more steps can be omitted. For example, as depicted in FIG. 5B and with reference to FIG. 4, in an exemplary procedure in accordance with the arrangement 300 of FIG. 3, an exemplary system: at 521, receives user input identifying individual skin feature(s) in the first image (in which case, the specification of an ROI can be omitted); at 530, predicts the location(s) in the second image of the skin feature(s) detected in the first image; at 551, receives user input identifying individual skin feature(s) in the second image; at 560 identifies any correspondence(s) unchanged, missing, and/or changed; and at 570 generates indications of such correspondence relationships (e.g., unchanged, missing, changed), as described above.

Figure 5C:
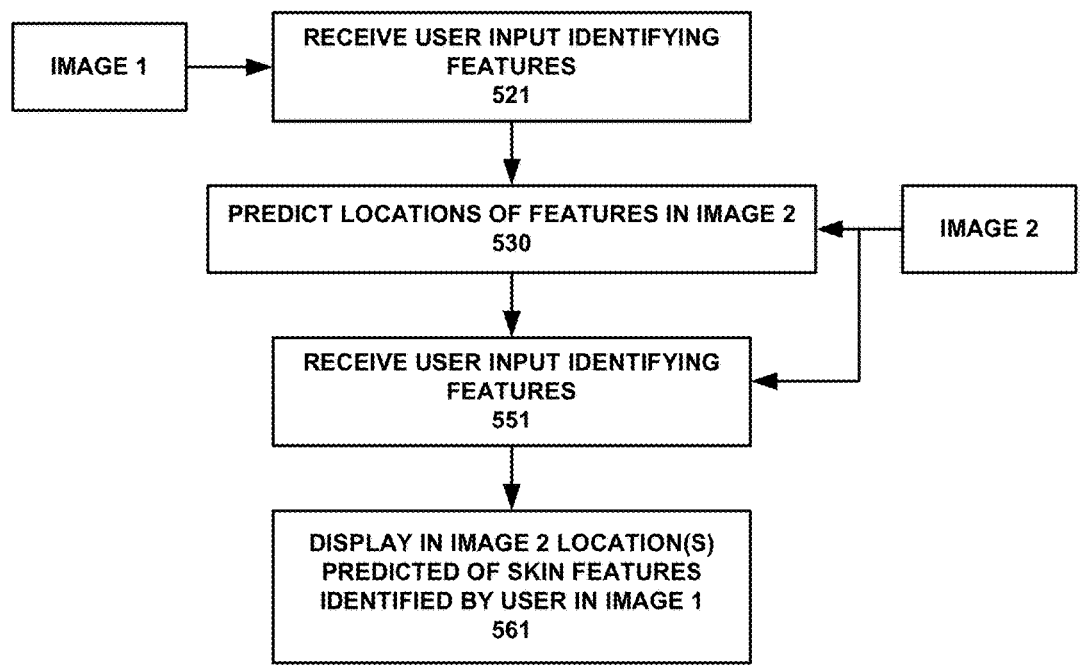

As depicted in FIG. 5C and with reference to FIG. 4, in another exemplary procedure in accordance with the arrangement 300 of FIG. 3, an exemplary system: at 521, receives user input identifying individual skin feature(s) in the first image (in which case, the specification of an ROI can be omitted); at 530, predicts the location(s) in the second image of the skin feature(s) detected in the first image; at 551, receives user input identifying individual skin feature(s) in the second image; and at 561, receives user input specifying the correspondence (if any) between the skin feature(s) identified in steps 521 and 551. Preferably, to assist the user with this step, the system displays in or on the second image the location(s) predicted in step 530 of the skin feature(s) identified by the user in the first image. For example, as shown in FIG. 4, P3 indicates the location in Image 2 predicted in step 3 for feature F3.

Figure 5D:
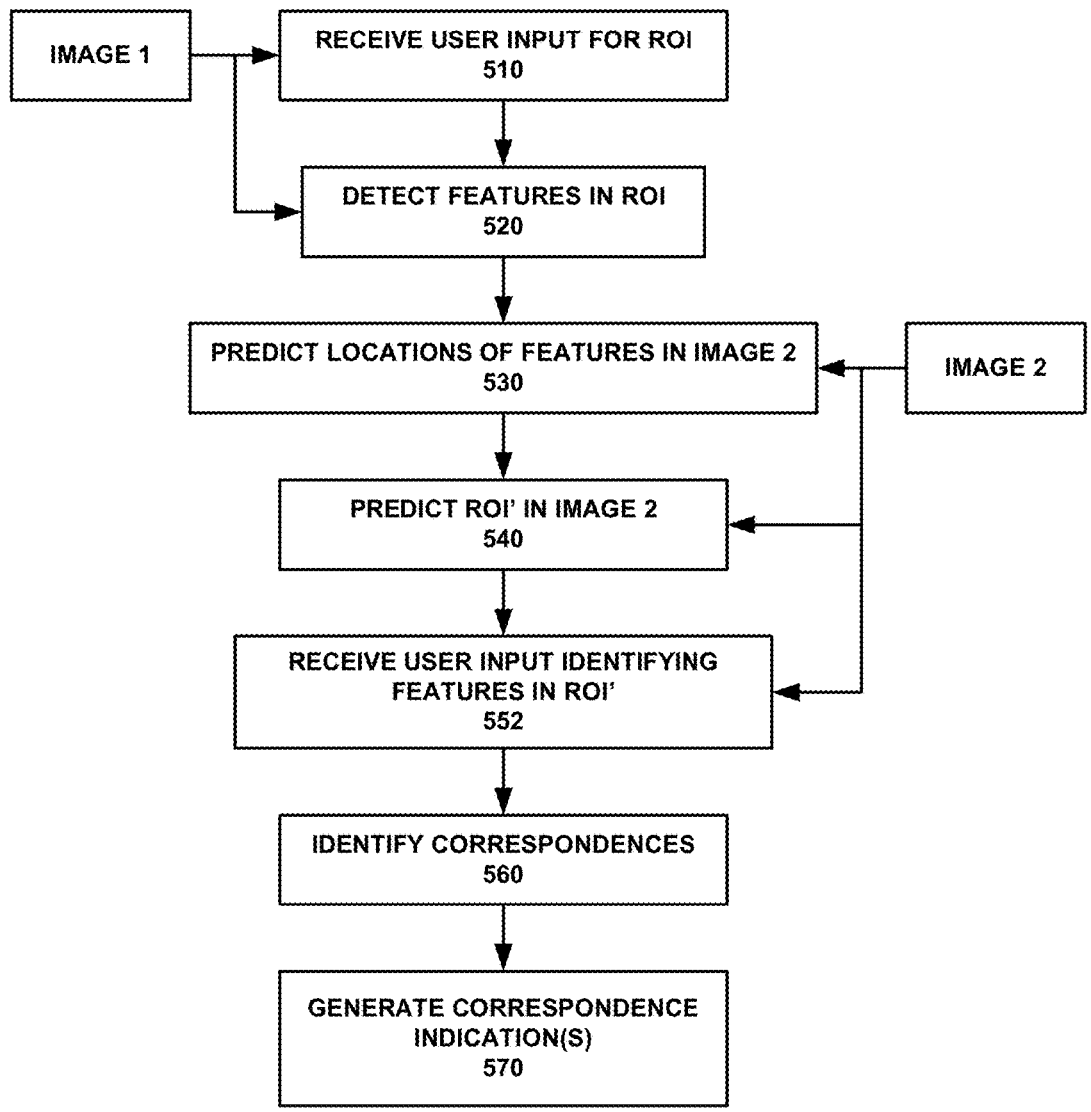

As depicted in FIG. 5D and with reference to FIG. 4, in another exemplary procedure in accordance with the arrangement 300 of FIG. 3, an exemplary system: at 510-540, operates as described above; at 552, receives user input identifying individual skin feature(s) in the second image within the predicted ROI' in the second image; and at 560 and 570 operates as described above.

Figure 5E:
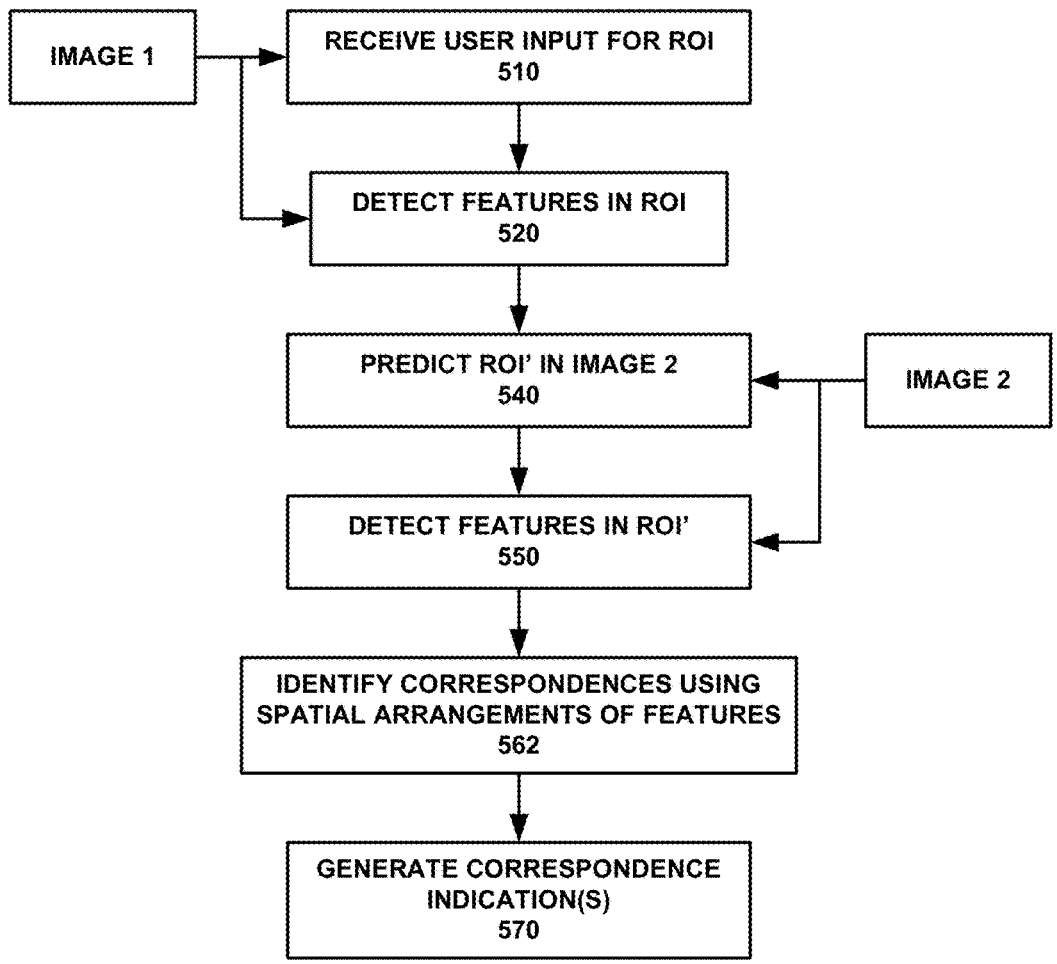

As depicted in FIG. 5E and with reference to FIG. 4, in another exemplary procedure in accordance with the arrangement 300 of FIG. 3, an exemplary system: operates as described above with respect to steps 510-550; at 562, uses the spatial arrangement of skin feature(s) detected at 520 and the spatial arrangement of skin feature(s) detected at 550 to determine existing correspondence(s) and identify missing correspondence(s)/skin feature(s); and generates correspondence indications at 570, as described above.

The above described embodiments are useful in identifying the progression/regression of skin features. An exemplary advantageous use of embodiments of the present disclosure entails computing motion for consecutive image pairs of a capture sequence in a pair-wise sliding window fashion. In this case, the predictions from one image pair to the next can be daisy-chained so that the system will automatically generate a spatio-temporal sequence of one or more features of interest in a user-specified ROI as the feature(s) evolve over time. In some cases, however, motion can be further computed using other possible groupings of images such triplets, quadruplets, etc. but the overall process would still be retained and the results of the processing daisy-chained accordingly.

Preferably, the system can also generate and display statistics related to changes in one or more of the color, intensity, shape, border, size or texture of a skin feature, which could help the user analyze the feature from its onset to its termination. Additionally, with the use of linear or non-linear regression models, the system can also preferably extrapolate the changes and simulate various "what-if" scenarios that might play out in the future. Preferably, this temporal data sequence (image and change statistics) can be coupled with a 3D system to provide topographical changes and/or with high-resolution dermoscopy for detailed textural changes, both of which would provide additional information helpful to the user.

While conventional white light images may be shown in FIG. 4 for illustrative purposes, it bears repeating that the present disclosure contemplates that the images may differ in modality and device of capture. Consider the example of a feature that appears as a hemoglobin blob in the first image and the second image is a green fluorescence image. In attempting to determine the correspondence relationship of the feature's appearance in the first image and the feature's appearance in the second image, the location of the feature in the second image is predicted, as described above, based on the location of the hemoglobin blob in the first image. The appearance of the feature in the second image is searched for by detecting any fluorescence signal at or proximate to the predicted location.

Additionally, it bears noting that in other embodiments or scenarios at least one of the images may be derived from other images or computed from other data, as opposed to being directly captured by a camera or other image capture device. As such, when comparing images across devices or modalities, it is contemplated by the present disclosure that at least one of the appearances of a feature may be a derived measurement. Thus for example, the first image may be a 2D representation of hemoglobin concentration over an area of skin and the second image may represent topography from a 3D surface.

It should be noted that in the above-described implementations in accordance with the present disclosure, the pixel values in the original images are preferably not warped or interpolated using the estimated motion. Preferably, copies of the original images are warped for the purposes of parameter estimation and the warped copies can be discarded after the process is completed, or can be retained, in order, for example, to provide the user with a virtual simulation of the change for better visualization. Preferably, the as-captured images, and not the copies modified by the motion estimation process, are the images used for any predictive data analytics to be determined.

As mentioned above, the sequence of images processed in accordance with the present disclosure can represent two or more images captured under different imaging modalities, at different times (including, for example, individually captured single images, or frames in a video sequence), with different devices, or any combination of these three dimensions of variation depicted graphically in FIG. 1, namely, 1) the imaging devices that are used, 2) the imaging modalities that the subject is captured under, and 3) the timepoints at which the images are captured. The three-dimensional space of FIG. 1 can be thought of as representing various feature tracking use cases to which embodiments of the present disclosure can be applied. From a processing perspective, the captured images in each dimension can either be used exclusively or in tandem with images from other dimensions. The multiple dimensions allow for various possible combinations of use cases, which could include, but are not limited to, the following illustrative variants.

Case 1: the imaging modality changes between the input images while the timepoint and the type of device used remain the same.

A. A doctor uses a 2D capture system (e.g., Canfield Scientific Inc.'s VISIA) to capture multiple images of a subject using different lighting modalities. However, changes in facial expression, subject's breathing, etc., will result in small deformations between any two successive captures. In this case, it may be necessary to compensate for the observed motion to identify collocated pixels across the different imaging modalities.

B. The doctor uses a dermatoscope to capture a cross-polarized image and a standard white light image of a skin lesion. However, the motion between the two images might have to be compensated to account for the subject's movement and/or the doctor's motion when placing the dermatoscope on the subject.

Case 2: the type of device and the imaging modality change while the timepoint remains the same.
   A. The doctor captures a 3D image of a subject using a whole body system. During the same visit, the doctor also uses a dermatoscope to capture cross-polarized images of lesions on the subject. The lesions captured with the dermatoscope are compared with the lesions detected in the 3D model, and automatically aligned and tagged with the lesions on the 3D model that provide for the best possible match (auto-tagging).
   B. The doctor captures a fluorescence image of a skin lesion using a 2D capture system (e.g., Canfield Scientific Inc.'s VISIA) and follows it with a localized cross-polarized image using a dermatoscope. Due to differences in scale and the spatial positioning of the two devices, an auto-tagging and alignment process between the two images can be advantageously performed.

Case 3: the imaging modality and timepoint change while the device remains the same.
   The doctor uses a 2D capture system (e.g., Canfield Scientific Inc.'s VISIA) to capture multiple images of a subject using different lighting modalities (e.g., standard white light, cross-polarized, parallel-polarized, fluorescence, etc.) and over multiple visits. A challenge here is to compensate for large appearance changes (like skin tone variations due to changes in lifestyle) in addition to the small scale movements that occur between two intra-modality captures. In this case, it may be necessary to independently compensate the motion across time, and this result combined with the intra-modality motion to quantify the overall motion across modality and time.

Case 4: the timepoint changes while the device and modality remain the same.
   A. The doctor uses a 3D imaging system (e.g., Canfield Scientific Inc.'s VECTRA) or a whole body system (e.g., Canfield Scientific Inc.'s WB360) to capture white light images of the subject over a period of multiple visits. Since the subject cannot be expected to maintain the exact pose across all of the captures, the system would need to compensate for the observed changes in pose between any two captures, in addition to identifying collocated pixels across time.
   B. The doctor uses a 2D image capture system (e.g., Canfield Scientific Inc.'s VISIA) to capture cross-polarized images of a subject with a skin condition, like Rosacea, over a period of multiple visits. The doctor could then use the cross-polarized image sequence to observe and visualize the sub-dermal changes occurring due to the progression of Rosacea.

Case 5: the imaging modality, type of device used, and capture timepoints change.
   The doctor uses a 3D imaging system (e.g., Canfield Scientific Inc.'s VECTRA or WB360 system) to monitor a subject over multiple visits. During each visit, the subject is captured using the 3D imaging system and correspondences are established between lesions across all the available visits. Based on the temporal changes in lesion statistics (both intra-lesion changes and changes observed in neighboring lesions), specific lesions can be brought to the attention of the doctor who could then use dermoscopy to continue monitoring the evolving lesions. Moving forward, each time a cross-polarized dermoscopy image of a lesion is captured, it is auto-tagged to a lesion on the 3D system, and appended to the collection of images of the lesion under consideration. Whenever required, the doctor could extract the collection of images for display, which could include the dermoscopy images, the 2D images from the 3D model, and possibly the 3D surface of the lesion. All the data would be aligned to one another so that the doctor could manually visualize temporal changes (color, texture, border, volume, etc.) from the data. As a diagnostic aid for the doctor, the system might also be able to automatically highlight changes inside the lesion (color or textural segmentation), and/or extrapolate the changes to a future possible time. For example, the system could measure the area of a lesion over time, and predict its area at a future point using model-fitting strategies.

Figure 6:
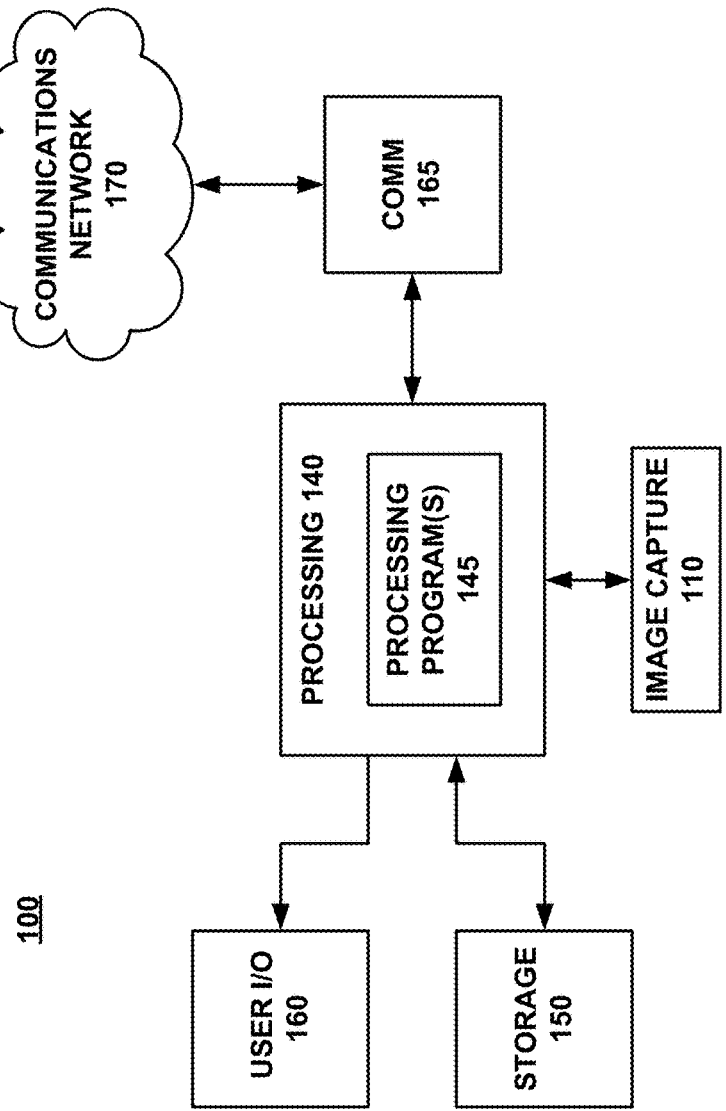
FIG. 6 is a schematic representation of an exemplary system in accordance with the present disclosure.

Turning now to FIG. 6, there is shown in schematic form an exemplary skin imaging system 100 in accordance with the present disclosure. As shown in FIG. 6, components of system 100 include an image capture system 110 coupled to a processing module 140. Image capture system 110 may include one or more hand-held or mounted point-and-shoot or DSLR cameras, mobile cameras, frontal or rear-facing smart-device cameras, dermatoscopes (e.g., Canfield Scientific Inc.'s VEOS), 2D skin imaging systems (e.g., Canfield Scientific Inc.'s VISIA), 3D human body imaging devices (e.g., Canfield Scientific Inc.'s VECTRA), and/or 3D Total Body systems (e.g., Canfield Scientific Inc.'s WB360), 3D volumetric imaging devices, among others.

Advantageously, the captured images can be single mode or multimodal--including, for example, those from standard white light, polarized light, and/or fluorescent light--captured at selected wavelengths and/or illuminated with selected wavelengths of light.

Images captured by image capture system 110 are provided to processing module 140 for processing as described above. Of further advantage, processing module 140 may also control image capture system 110, for example, by controlling one or more aspects of the image capture and/or illumination of the subject, such as exposure, modality, or filtering, among others.

Images may also be provided to processing module 140 from other sources and by other means. For example, images may be provided via communications network 170, or in a non-transient storage medium, such as storage 150.

Processing module 140 may be coupled to storage 150, for storing and retrieving images and motion models, among other data, and to input/output devices 160, such as a display device and/or user input devices, such as a keyboard, mouse, or the like. Processing module 140 may also be coupled to a communications module 165 for interconnection with a communications network 170, such as the Internet, for transmitting and receiving images and/or data, and/or receiving commands, software updates or the like. Processing module 140, storage 150, I/O 160, and/or communications module 165 may be implemented, for example, with one or more computers, workstations, or the like, operating in accordance with one or more programs 145 embodied in a compatible, non-transient, machine-readable storage medium.

It should be noted that the exemplary system 100 illustrates just one of a variety of possible arrangements contemplated by the present disclosure. For example, the various modules of system 100 need not be co-located. For example, image capture system 110 and I/O devices 160 can be located in a dermatologist's office and processing module 140 and storage module 150 can be remotely located, functioning within a tele-dermatology framework, or "cloud-based," interacting with image capture system 110 and I/O devices 160 over communications network 170. In other exemplary arrangements, I/O devices 160 can be remotely located from image capture system 110, thereby allowing a dermatologist to remotely examine a subject's skin.

At this point, while this disclosure has been presented using some specific examples, those skilled in the art will recognize that the teachings of this disclosure are not thus limited. Accordingly, this disclosure should be only limited by the scope of the claims attached hereto.

What is claimed:

1. A method performed by a skin imaging apparatus comprising:
receiving first and second images including an area of skin, wherein the first and second images differ in at least one of a time, a device, a field of view, a scale, an illumination and a modality of capture;
determining a first appearance of a skin feature in the first image;
searching for a second appearance of the same, or a related, skin feature in the second image;
determining for the skin feature a correspondence relationship between the first and second images based on the first appearance and the search for the second appearance including predicting a location of the skin feature in the second image and using the predicted location to determine the correspondence relationship; and
controlling a display device to display at least one of the first and second images so as to indicate the correspondence relationship.

2. The method of claim 1, wherein determining the first appearance of the skin feature in the first image includes at least one of detecting the first appearance of the skin feature in the first image and receiving user input indicative of the first appearance of the skin feature in the first image.

3. The method of claim 1, wherein the correspondence relationship includes an unchanged correspondence, a missing correspondence, or a changed correspondence.

4. The method of claim 1, wherein searching for the second appearance of the skin feature includes searching at the predicted location of the same, or a related, skin feature in the second image.

5. The method of claim 1, wherein predicting the location of the skin feature in the second image includes:
determining a parametric motion model; and
performing at least one of a spatial and a temporal analysis using the parametric motion model to predict the location of the skin feature in the second image.

6. The method of claim 5, wherein determining the parametric motion model includes one or more of performing: image pre-processing on at least one of the first and second images, pose estimation, global scale motion estimation, intermediate scale motion estimation and local scale motion estimation.

7. The method of claim 1 comprising:
receiving user input identifying a region of interest in the first image,
wherein the first appearance of the same, or a related, skin feature is detected in the region of interest.

8. The method of claim 7 comprising:
predicting a location of the region of interest in the second image,
wherein searching for the second appearance of the same, or a related, skin feature includes searching in the predicted location of the region of interest in the second image.

9. The method of claim 1 comprising:
determining a measurement associated with the skin feature; and
controlling the display device to display an indication of the measurement.

10. A non-transitory computer-readable storage medium having stored thereon a computer program comprising instructions for causing the skin imaging apparatus to perform the method of claim 1.

11. A skin imaging apparatus comprising:
a storage device containing instructions; and
a processor for executing the instructions to:
receive first and second images including an area of skin, wherein the first and second images differ in at least one of a time, a device, a field of view, a scale, an illumination, and a modality of capture;
determine a first appearance of a skin feature in the first image;
search for a second appearance of the same, or a related, skin feature in the second image;
determine for the skin feature a correspondence relationship between the first and second images based on the first appearance and the search for the second appearance, including predicting a location of the skin feature in the second image and using the predicted location to determine the correspondence relationship; and
control a display device to display at least one of the first and second images so as to indicate the correspondence relationship.

12. The apparatus of claim 11, wherein determining the first appearance of the skin feature in the first image includes at least one of detecting the first appearance of the skin feature in the first image and receiving user input indicative of the first appearance of the skin feature in the first image.

13. The apparatus of claim 11, wherein the correspondence relationship includes an unchanged correspondence, a missing correspondence, or a changed correspondence.

14. The apparatus of claim 11, wherein searching for the second appearance of the skin feature includes searching at the predicted location of the same, or a related, skin feature in the second image.

15. The apparatus of claim 11, wherein predicting the location of the skin feature in the second image includes:
determining a parametric motion model; and
performing at least one of a spatial and a temporal analysis using the parametric motion model to predict the location of the skin feature in the second image.

16. The apparatus of claim 15, wherein determining the parametric motion model includes one or more of performing: image pre-processing on at least one of the first and second images, pose estimation, global scale motion estimation, intermediate scale motion estimation and local scale motion estimation.

17. The apparatus of claim 11, wherein the storage device contains instructions for execution by the processor to:
receive user input identifying a region of interest in the first image,
wherein the first appearance of the skin feature is detected in the region of interest.

18. The apparatus of claim 17, wherein the storage device contains instructions for execution by the processor to:
predict a location of the region of interest in the second image,
wherein searching for the second appearance of the skin feature includes searching in the predicted location of the region of interest in the second image.

19. The apparatus of claim 11, wherein the storage device contains instructions for execution by the processor to:
   determine a measurement associated with the skin feature; and
   control the display device to display an indication of the measurement.

20. The method of claim 1, comprising altering at least one of the first and second images and controlling the display device to display a combination of the first and second images.

21. The apparatus of claim 11, wherein the storage device contains instructions for execution by the processor to:
   alter at least one of the first and second images; and
   control the display device to display a combination of the first and second images.

22. The method of claim 1, comprising predicting a location of the skin feature in a third image, including:
   determining a parametric motion model using the first and second images; and
   performing at least one of a spatial and a temporal analysis using the parametric motion model to predict the location of the skin feature in the third image.

23. The apparatus of claim 11, wherein the storage device contains instructions for execution by the processor to predict a location of the skin feature in a third image, including:
   determining a parametric motion model using the first and second images; and
   performing at least one of a spatial and a temporal analysis using the parametric motion model to predict the location of the skin feature in the third image.

24. The method of claim 1, wherein each of the first and second images is captured with a device including a whole-body imaging system, a partial body imaging system, a hand-held or mounted point-and-shoot or DSLR camera, a mobile device camera, a 2D skin imaging system, a 3D imaging system, or a dermatoscope.

25. The apparatus of claim 11, wherein each of the first and second images is captured with a device including a whole-body imaging system, a partial body imaging system, a hand-held or mounted point-and-shoot or DSLR camera, a mobile device camera, a 2D skin imaging system, a 3D imaging system, or a dermatoscope.

* * * * *